(12) United States Patent
Gibson et al.

(10) Patent No.: US 12,427,241 B2
(45) Date of Patent: Sep. 30, 2025

(54) SYSTEMS AND METHODS FOR DRUG DELIVERY

(71) Applicant: AMGEN INC., Thousand Oaks, CA (US)

(72) Inventors: Scott R. Gibson, Thousand Oaks, CA (US); Xiaotong Li, Simi Valley, CA (US); Nicholas J. Clark, Thousand Oaks, CA (US); Carsten Bech, Thousand Oaks, CA (US); Daniel Rojecki, Copenhagen (DK); Joshua Jay Dudman, Copenhagen (DK); Jakob Pedersen, Frederiksberg (DK); Jennifer L. Sawicky, Thousand Oaks, CA (US); Laura Watson, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 829 days.

(21) Appl. No.: 17/770,326

(22) PCT Filed: Oct. 14, 2020

(86) PCT No.: PCT/US2020/055459
§ 371 (c)(1),
(2) Date: Apr. 20, 2022

(87) PCT Pub. No.: WO2021/080822
PCT Pub. Date: Apr. 29, 2021

(65) Prior Publication Data
US 2022/0387700 A1 Dec. 8, 2022

Related U.S. Application Data (60) Provisional application No. 62/925,634, filed on Oct. 24, 2019.

(51) Int. Cl.
*A61M 5/00* (2006.01)
*A61J 1/10* (2006.01)
(Continued)

(52) U.S. Cl.
CPC ............ *A61M 5/002* (2013.01); *A61J 1/10* (2013.01); *A61J 1/2024* (2015.05); *A61J 1/2093* (2013.01); *A61M 5/14* (2013.01); *G16H 20/17* (2018.01)

(58) Field of Classification Search
CPC ........ A61M 5/002; A61M 5/14; A61J 1/2024; A61J 1/10; A61J 1/2093; G16H 20/17
(Continued)

(56) References Cited

U.S. PATENT DOCUMENTS

| | | | |
|---|---|---|---|
| 4,522,302 A | * | 6/1985 | Paikoff ................. A61M 5/003 206/570 |
| 4,722,733 A | | 2/1988 | Howson |

(Continued)

FOREIGN PATENT DOCUMENTS

| | | |
|---|---|---|
| CN | 108335412 A | 7/2018 |
| WO | WO-2011139921 A2 | 11/2011 |

OTHER PUBLICATIONS

Written Opinion of the International Searching Authority issued to International Application No. PCT/US2020/055459, dated Feb. 4, 2021.
(Continued)

*Primary Examiner* — Jacob K Ackun
(74) *Attorney, Agent, or Firm* — MARSHALL, GERSTEIN & BORUN LLP; Michael P. Furmanek (57) ABSTRACT

A drug delivery system includes a packaging housing a first component including at least one of a drug product, a diluent, a saline solution, or an IV stabilizing solution ("IVSS") and a second component comprising at least one of the drug product, the diluent, the saline solution, and the IVSS, the first component being different than the second component. The first component is disposed in a first container in a storage state and the first container is positioned in a first compartment of the packaging housing. The second component is disposed in a second container in a storage state and the second container is positioned in a second compartment of the packaging housing. At least one of the first compartment and the second compartment may include an individual seal and wherein each of the individual seals and the first and second compartments are sterilized.

5 Claims, 6 Drawing Sheets

(51) Int. Cl.
*A61J 1/20* (2006.01)
*A61M 5/14* (2006.01)
*G16H 20/17* (2018.01)

(58) Field of Classification Search
USPC .......................................... 206/570, 571, 438
See application file for complete search history.

(56) References Cited

U.S. PATENT DOCUMENTS

| | | | | |
|---|---|---|---|---|
| 5,178,282 | A * | 1/1993 | Williams | A61B 50/30 |
| | | | | 206/370 |
| 6,000,548 | A * | 12/1999 | Tsals | A61B 50/33 |
| | | | | 206/570 |
| 6,779,566 | B2 * | 8/2004 | Engel | A45D 40/00 |
| | | | | 141/330 |
| 6,935,133 | B2 * | 8/2005 | Keeter | A61M 5/003 |
| | | | | 62/457.2 |
| 2003/0075474 | A1 * | 4/2003 | Moyer | A61B 50/33 |
| | | | | 206/570 |
| 2007/0158519 | A1 * | 7/2007 | Coe | A61J 7/0069 |
| | | | | 206/570 |
| 2008/0141700 | A1 * | 6/2008 | Fuchs | F25D 3/08 |
| | | | | 206/570 |
| 2009/0236259 | A1 * | 9/2009 | Hicks | A61B 50/30 |
| | | | | 206/570 |
| 2010/0274205 | A1 | 10/2010 | Morelli et al. | |
| 2012/0267272 | A1 * | 10/2012 | Agrawal | A61B 50/30 |
| | | | | 206/439 |
| 2013/0313156 | A1 * | 11/2013 | Duncan | B65D 1/36 |
| | | | | 206/570 |

OTHER PUBLICATIONS

International Search Report issued to International Application No. PCT/US2020/055459, dated Feb. 4, 2021.

* cited by examiner

SYSTEMS AND METHODS FOR DRUG DELIVERY

CROSS-REFERENCE TO RELATED APPLICATION

This is the United States national phase of International Patent Application No. PCT/US20/55459, filed Oct. 14, 2020, which claims priority to U.S. Application No. 62/925,634, filed Oct. 24, 2019, the entire contents of each of which are hereby incorporated by reference herein.

FIELD OF DISCLOSURE

The present disclosure generally relates to drug delivery systems and methods and, more particularly, to approaches for drug delivery systems and methods including multiple components.

BACKGROUND

Drugs are administered to treat a variety of conditions and diseases. Intravenous ("IV") therapy is a drug dosing process that delivers drugs directly into a patient's vein using an infusion contained in a delivery container (e.g., a pliable bag). These drug dosings may be performed in a healthcare facility, or in some instances, at remote locations such as a patient's home. In certain applications, a drug product may be shipped to a healthcare facility (e.g., an inpatient facility, an outpatient facility, and/or a pharmacy) in a powdered or lyophilized form.

When reconstituting these drugs for administration, it is of particular importance to maintain a sterile environment so as to not taint or otherwise damage the quality of the drug. Additionally, some classes of drugs such as bi-specific T-cell engagers may require exceptionally accurate quantities of the drug product and/or other fluids required for dosing so as to prevent the drug product from becoming toxic. Oftentimes, the healthcare professional must prepare the drug by closely following a set of steps to ensure a sterile environment is maintained and that correct quantities of ingredients are added to the delivery container. When reconstituting these drugs for administration, it may be desirable or necessary to utilize a diluent, such as by adding a diluent to a drug product vial. As a result of these various steps and requirements, the reconstitution process may be time-consuming, tedious, and may have an unacceptable or undesirable error rate.

The current process of reconstituting a lyophilized oncology product is often performed either at the hospital or the specialty compounding pharmacy by a licensed pharmacist. The use of a hood is often required to perform reconstitution steps to provide a sterile working environmental which can be cumbersome for pharmacist given the complexity of the steps. In addition, this reconstitution process involves the use of multiple needles to withdraw/add sterile water for injection (WFI), saline and/or Intravenous Solution Stabilizer (IVSS) solutions. Typically, for relatively complex oncology products such as a Bi-specific T-cell Engager (BITE®) molecule (e.g. Blincyto®) prepared in an IV bag, a specified volume of WFI is added to reconstitute a lyophilized drug product contained in a vial via the use of a needle and syringe system. Then, the applicable volume of saline and IVSS solutions are added to an empty IV bag before the final reconstituted drug product is introduced. The overall process may involve relatively extensive manual labor time and steps.

As described in more detail below, the present disclosure sets forth systems and methods for drug delivery and/or preparation system embodying advantageous alternatives to existing systems and methods, and that may address one or more of the challenges or needs mentioned herein, as well as provide other benefits and advantages.

SUMMARY

In a first embodiment, a drug delivery system includes a packaging housing a first component including at least one of a drug product, a diluent, a saline solution, or an IV stabilizing solution ("IVSS") and a second component comprising at least one of the drug product, the diluent, the saline solution, and the IVSS, the first component being different than the second component. The first component is disposed in a first container in a storage state and the first container is positioned in a first compartment of the packaging housing. The second component is disposed in a second container in a storage state and the second container is positioned in a second compartment of the packaging housing. At least one of the first compartment and the second compartment may include an individual seal and wherein each of the individual seals and the first and second compartments are sterilized.

The drug delivery system may also include a third component selected from a group of the drug product, the diluent, the saline solution, and the IVSS, wherein the third component is different than the first component and the second component, wherein the third component is in a third container in a storage state and the first container is positioned in a third compartment of the packaging housing.

The packaging housing may include a housing bottom surface, where at least one of the first, second, and third compartments has a compartment bottom surface that is non-parallel to the housing bottom surface to facilitate removal of air from the container.

At least one of the containers may be an IV bag. The packaging housing may include at least one port holder configured to secure at least one port of the IV bag in a storage position, and wherein the port holder is removable from the packaging housing to facilitate removal of the IV bag from the packaging housing. Additionally or alternatively, the port holder may be attached through a hinge-like connection to allow for the IV-ports to be secured during admixing and then the hinge may swivel to release the IV-bag port after admixing is complete.

A method of ordering a drug delivery system may be provided to a specified destination. The method may include providing a digital platform for ordering the drug delivery system; receiving user input including at least one of the following: duration of therapy, desired volume, infusion set used, travel dates, the location of the specified destination; and based on user input, automatically providing sufficient amounts of the drug delivery system to the specified destination.

BRIEF DESCRIPTION OF THE DRAWINGS

The above needs are at least partially met through provision of the systems and approaches for drug delivery device reconstitution described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure relates to a drug delivery and/or preparation system that provides the sterile environment that could enable an improved preparation environment, thereby reducing risk and the number of steps for preparation. As a more specific example, the present disclosure relates to a system and method that may offer benefits and/or precautions of a Closed System Transfer Device (CSTD), but while providing a disposable, portable, and user-friendly system or method.

Turning to the figures, pursuant to these various embodiments, a drug delivery system or kit 100 and a corresponding method of preparing a drug delivery device using the drug delivery system are provided. The drug delivery system 100 can be used by a healthcare professional, a caregiver, or patient to prepare a drug delivery device to be delivered to a patient. The drug delivery system 100 differs from conventional systems in that a number of the components included in the system 100 come prefilled and/or premixed in correct dosage quantities. As a result, necessary preparation of the drug delivery device by the healthcare professional, caregiver, or patient is reduced while still ensuring correct quantities of ingredients are administered. The system 100 may be used to provide intravenous, subcutaneous, intra-arterial, intramuscular, and/or epidural delivery approaches. By using the system 100, patient anxiety and or confusion may be reduced due to reduced preparation complexity and wait times caused by the drug preparation process. Additionally, the system 100 may permit a health care provider, a pharmacist, a patient, and/or other individuals involved in preparing, providing, or using medication to have a more streamlined, predictable, and/or effective process for drug delivery. For example, the system 100 may reduce the amount of time a pharmacist spends preparing medication for use by a patient, reduce the number of steps a pharmacist must manually take to prepare medication for use by a patient, and/or improve the overall efficiency of the medication preparation process. As a more specific example, the system 100 may be particularly advantageous for use with medication preparation that involves several steps, such as adding a diluent and then adding a solution containing saline and/or IVSS, and/or medication that requires extensive preparation time.

Figure 1A:
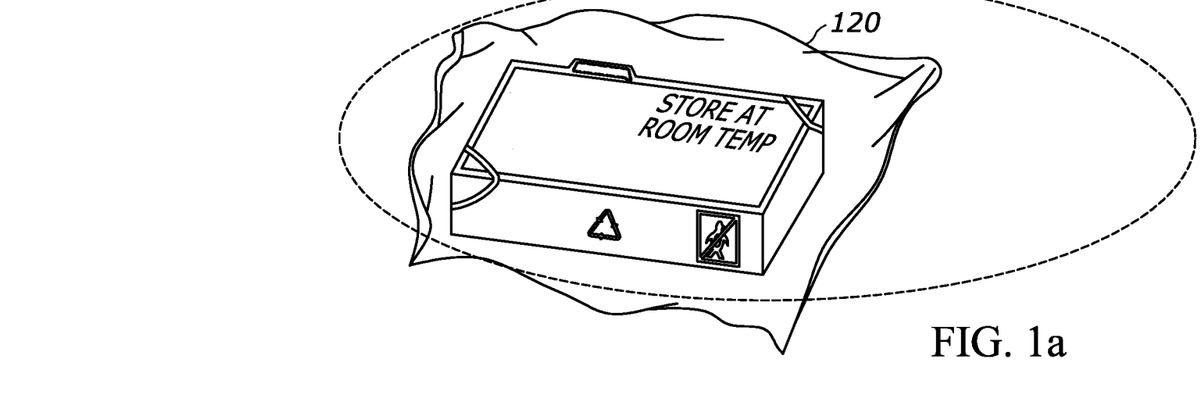
FIG. 1a illustrates an example first kit for an example drug delivery system in accordance with various embodiments.
Figure 1B:
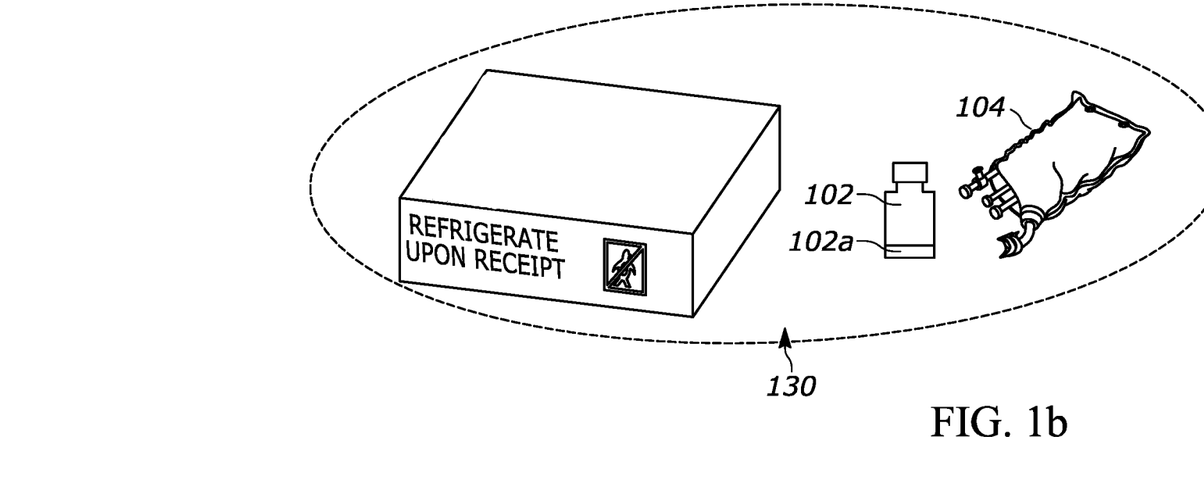
FIG. 1b illustrates an example second kit for an example drug delivery system in accordance with various embodiments.

The drug delivery system 100 may include a first container or kit 120 (FIG. 1a) and a second container or kit 130 (FIGS. 1b & 1c) which may be shipped separately from each other. Generally speaking, in some examples, the first kit 120 may include components that may be stored at room temperatures such as an admixture organization tray (140; FIG. 2a) and coupling components (e.g., a pre-filled syringe, a vial adapter, a needle, and/or a large syringe for air removal). Conversely, the second kit 130 may be in the form of a cold storage kit that includes components stored in refrigerated conditions, such as, for example, a drug product container 102 containing a drug product 102a (which, in some examples may be a lyophilized drug product), a saline container or IV bag 104 containing a saline solution 104a, and in some examples (FIG. 1c), a diluent (e.g., a preservative-free water for injection or "WFI") 106a disposed in a pre-filled syringe 106, a vial adapter 107 to couple the drug product container 120 with the saline container 104, and/or a needle 108 for use with the pre-filled syringe 106. In other examples, the pre-filled syringe 106, the vial adapter 107, and/or the needle 108 may be disposed within the first kit 120. As will be discussed, the first and second kits 120, 130 may be combined to form the system 100 by way of an admixture organization tray 140 (FIG. 2a) which may be included in the first kit 120. The first and/or second kits 120, 130 may include separate, discrete storage compartments to retain any of these and other components. In some examples, the first or second kits 120, 130 may further include an IV stabilizing solution ("IVSS") container containing an IVSS and a fluid path assembly (IV line) configured to selectively, fluidly couple or de-couple various of the aforementioned components.

The saline container 104 may be an IV bag, a vial, or any other suitable container. The saline container is coupled with the fluid path assembly via one or more ports. For example, IV spikes may pierce the ports to physically connect the saline container 104 to the fluid path assembly.

Figure 1C:
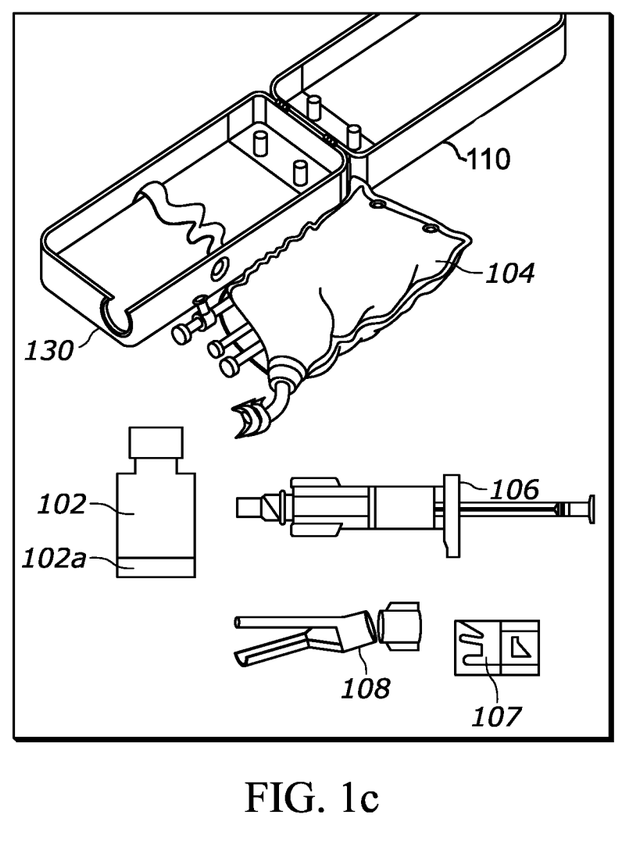
FIG. 1c illustrates the combined example first and second kits of FIGS. 1a and 1b in accordance with various embodiments.
Figure 2A:
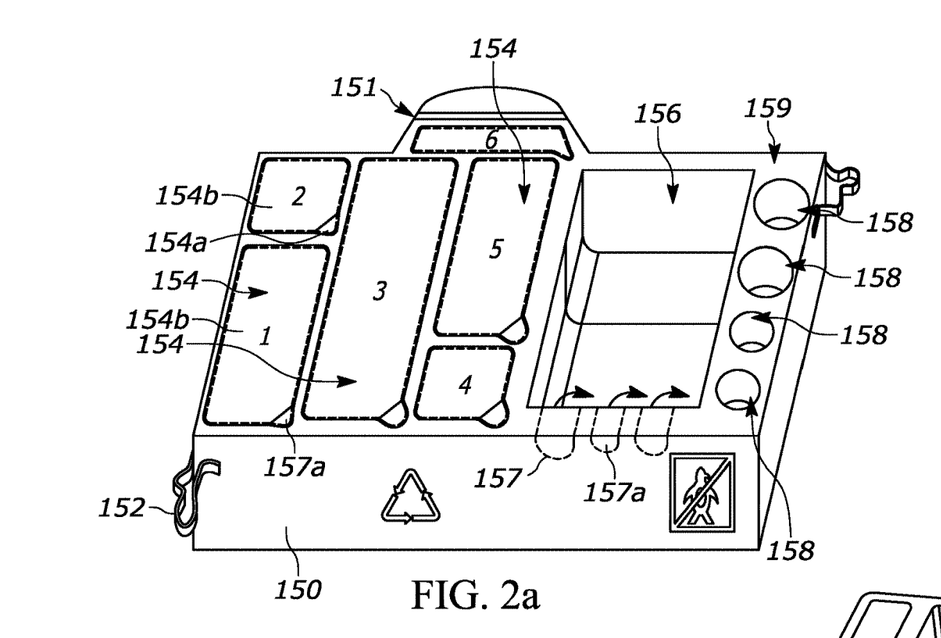
FIG. 2a illustrates an example admixture organization tray for use with the example drug delivery system of FIGS. 1a-1c in accordance with various embodiments.

With reference to FIG. 1c, the combined system 100 is provided and includes the drug product container 102 including the drug product 102a, a protector box 110, the prefilled IV bag 104 including an IVSS and saline solution, the prefilled syringe 106, the needle 108, and the vial adapter 107. Notably, the vial adapter 107 is a CSTD-like adapter to couple with the drug product container 102 to allow diluent addition for reconstitution of a lyophilized drug product and sterile and needle-less removal of the liquid drug product 102a from the container 102. The prefilled syringe 106 includes sterile water for injection or product-specific diluent. The needle 108 is coupled with a FirmCLICK or is modified to meet specifications associated with the CSTD version of the FirmClick prefilled syringe coupler for a healthcare professional who desires flexibility to admix into the IV vessel using a needle instead. The container 102 includes a FirmCLICK or modified CSTD version of the FirmCLICK prefilled syringe coupler is affixed to and manufactured with the IV bag 104 on the drug-add port thereof.

Turning to FIG. 2a, the system 100 may be provided in an optimized admixing container 150. More specifically, the container 150 may be in the form of a case that has a number of individually sealed wells or openings to receive the components for drug administration. The individually sealed wells or openings may be an arrangement of individually sealed blister pack containers that separate and organize admixing consumables, aids, and other components. The container 150 may come in a variety of sizes and have cutouts dimensioned to the size of the individual blister packs that may contain the components, which may vary based on region, to suit the requirements of certain healthcare facilities. In some examples, the container 150 may have openings dimensioned to receive each of the first and second kits 120, 130, and in other examples, the first and the second kits 120, 130 may be separate from the container 150. The container 150 may be constructed from a recyclable material that may be double sealed and sterile, though other examples are possible. The container 150 may include a stand 151 in the form of a channel to receive instructions for use in the form of a card that provides a visual representation of the admixing process, and may also include any number of retention mechanisms 152. The container 150 further includes any number of sterile, individually sealed component wells 154, each of which having a removable seal 154a and an indicator 154b to indicate an order in which components should be opened and removed.

The container 150 further includes a sloped IV bag well 156 having a shallow end 156a and a deep end 156b. The bag is sloped so as to aid with air removal. In some examples, the IV bag well 156 may have an angle of approximately 30°, though other examples are possible. The IV bag 104 is positioned in the IV bag well 156 to facilitate removal of air (by gravity). For example, the packaging housing bottom wall (which rests on a table or other surface) is preferably non-parallel with a bottom surface of the well 156 for the IV bag 104 so that air is urged towards the IV ports and can be more easily purged therefrom.

Figure 2B:
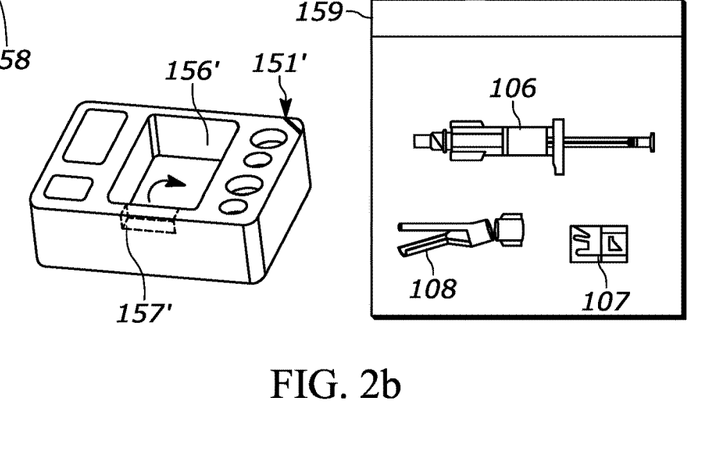
FIG. 2b illustrates an alternative example admixture organization tray for use with the example drug delivery system of FIGS. 1a-1c in accordance with various embodiments.

The container 150 further includes any number of IV bag port cut-outs 157 and holders/clasps 157a to assist with coupling components to the IV bag 104. The container 150 further includes any number of vial wells 158 of assorted sizes as well as a compartment 159. These wells 154, 156, 158 may be used to conveniently handle and stabilize the containers during admixture, and may have varying spacing and sizes as needed. With reference to FIG. 2b, in an alternative example, the IV bag port cut-out 157' may be provided in a hinged arrangement. Further, the container 150 may include slots 151' on each corner to partially insert and secure the instructions for use.

Figure 3:
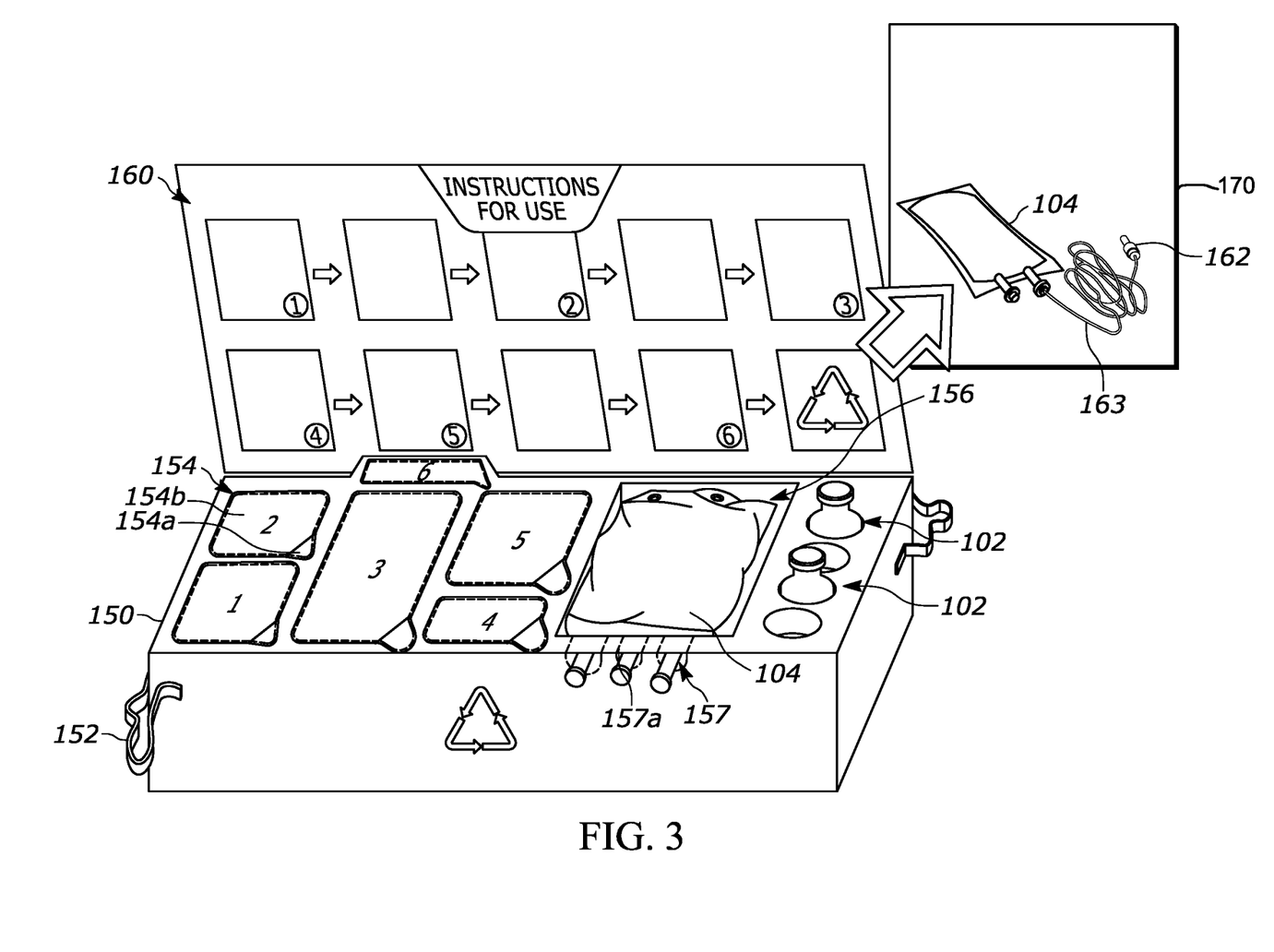
FIG. 3 illustrates the example admixture organization tray of FIG. 2a prior to admixture in accordance with various embodiments.

Turning to FIG. 3, an assembled kit 150 is provided that includes instructions 160 coupled to the container 150 via the stand 151. Further, in FIG. 3, the container 150 has the specific components disposed within the wells 154, 156, 158. The wells 154, 156, 158 are individually sealed and accessed during administration, and all components may be sterilized simultaneously and double sealed. The instructions 160 provide a step-by-step process for admixture. The numbered component wells 154 may include any number or quantity of prefilled syringes 106 with the desired volume of diluent (e.g., water for injection or bacteriostatic water for injection containing a preservative such as benzyl alcohol), a vial adapter 107 (e.g., a FirmCLICK or CSTD) for coupling the prefilled syringe 106 with the drug product container 102 for simplified reconstitution, a vial adapter-compatible vial spike 162 coupled with an IV line 163 (FIG. 4a), a disposable syringe adapter 163 (FIG. 4a), a large-volume disposable syringe (e.g., 60 mL) to remove residual air from the IV bag 104 (or other cartridge), and an IV-set filter unit (not illustrated) to be connected to the IV set upstream of the patient's infusion port. Other examples are possible. As illustrated in box 170, upon completion of admixture, the healthcare professional provides the prepared end product to an infusion nurse or other healthcare professional for infusion.

Figure 4A:
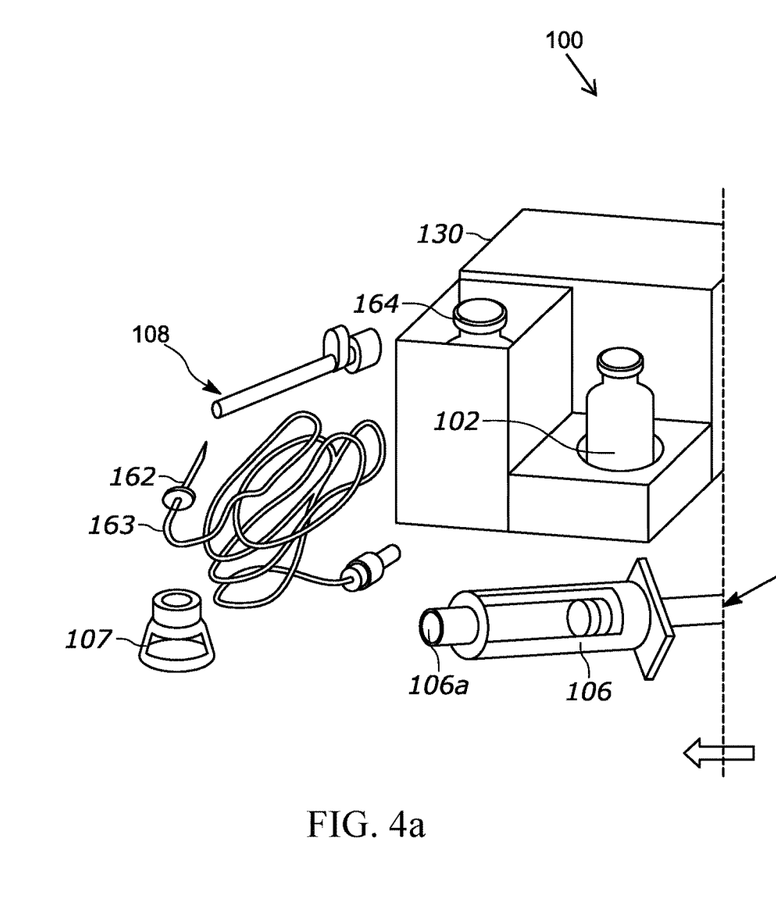
FIG. 4a illustrates the example second kit of the example drug delivery system of FIGS. 1a-3 in accordance with various embodiments.
Figure 4B:
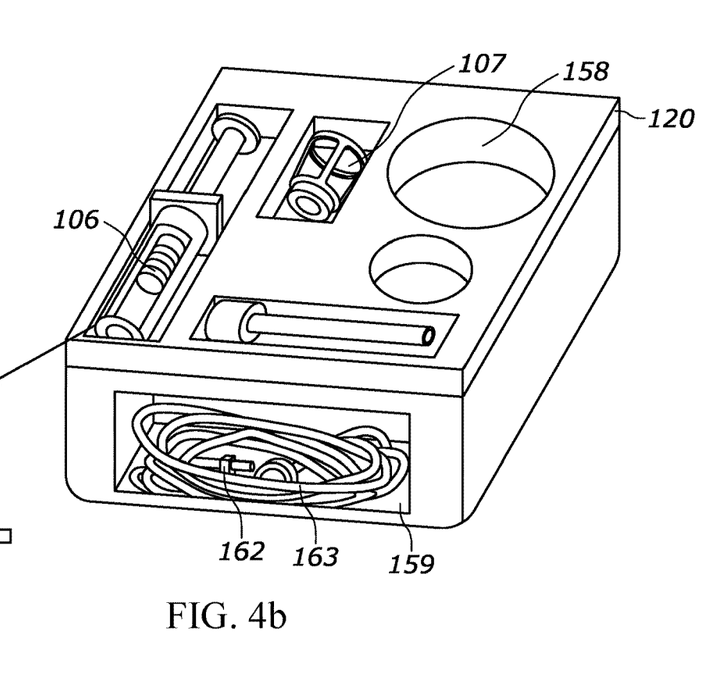
FIG. 4b illustrates the example first kit of the example drug delivery system of FIGS. 1a-3 in accordance with various embodiments.

With reference to FIGS. 4a and 4b, examples of first and second kits 120, 130 are provided, whereby components from the first kit 120 are being removed to couple with the components from the second kit 130. As previously stated, the first and second kits 120 (i.e., the room temperature storage kit including reconstitution, admixture, and administration components), 130 (i.e., the cold-storage packaging of drug product and IV bottle) may be combinable to form the container 150 or may separate kits from the container 150. In some examples, the second kit 130 may include the drug product container 102 and the saline bag 104. The first kit 120 may include the prefilled syringe 106 having a vial adapter coupler 106a, a vial adapter 107, and an IV line 163 coupled with a vial spike 162. Further, either one of the kits 120, 130 may include an IV bottle 164 including an IVSS-saline mixture for administration. As noted, these components may be disposed in any number of sterile, individually sealed components to help reduce or eliminate admixing errors and to reduce manual steps.

In some examples, the IV line 163 may include a tubing manifold having a series of connection points for physically connecting the respective containers with each other. As a more specific example, the connection points may include quick-connect sterile connectors with respective sub-components that selectively mate with each other while maintaining sterility or another desirable cleanliness standard. For example, the quick-connect sterile connectors may snap or twist or screw together; they may have sheathed or covered components that become unsheathed or uncovered upon connection; and/or they may have Luer Lock or modified Luer Lock configurations. As another example, the connectors may include one or more stake connectors for coupling one of the tube portions with an IV bag. The adaptors may be a closed system transfer device ("CSTD") or a suitable vial adaptor that matingly fits with the drug product container, which may be a vial. Similarly, the connector may be a vial adaptor that matingly fits with the diluent container, which may also be a vial. Similarly, the connector may be a vial adaptor that matingly fits with the IVSS container, which may be a vial. Any or all of the containers may be a vial with a standard septum that is pierced by a vial adapter or a vial stake; additionally or alternatively any or all of the containers may include a quick-connect sterile connector or other suitable connector. Alternatively, any or all of the containers may be a resilient container such as an IV bag or any other suitable container.

Continuous IV infusion therapy for oncology patients can extend for relatively long-term periods (e.g., 24 hours a day for 7 consecutive days). During continuous infusion, patients are tethered to their infusion pumps and the tubing sets/connections required to receive therapy. This may create a level of anxiety during their day to day activities, and this anxiety may be further exacerbated by the need to plan therapies around any travel plans. As such, the portal (app or web based) provides the ability to easily plan and obtain the therapies required during travel and actively informing patients' doctors is proposed.

Figure 5A:
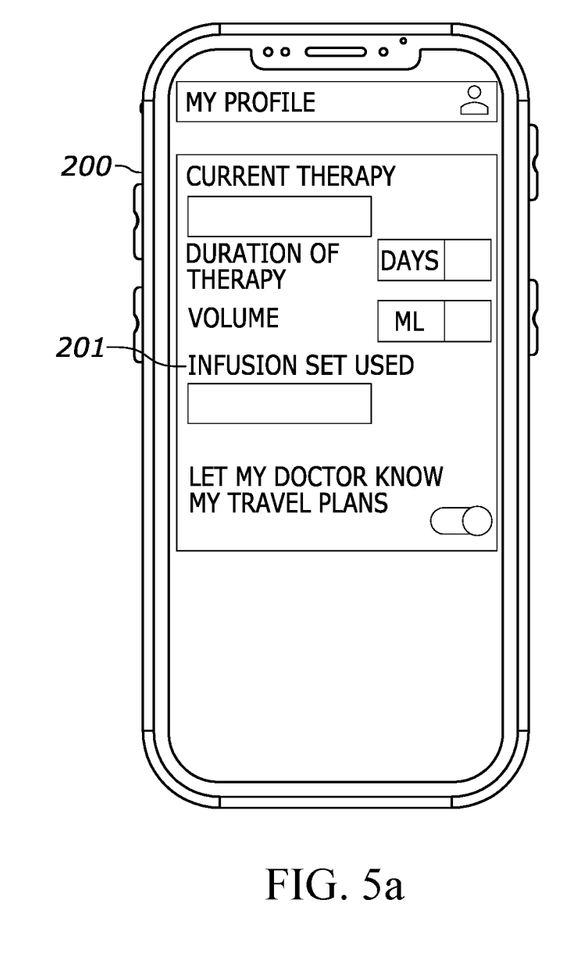
FIGS. 5a and 5b illustrate an example drug ordering system in accordance with various embodiments.
Figure 5B:
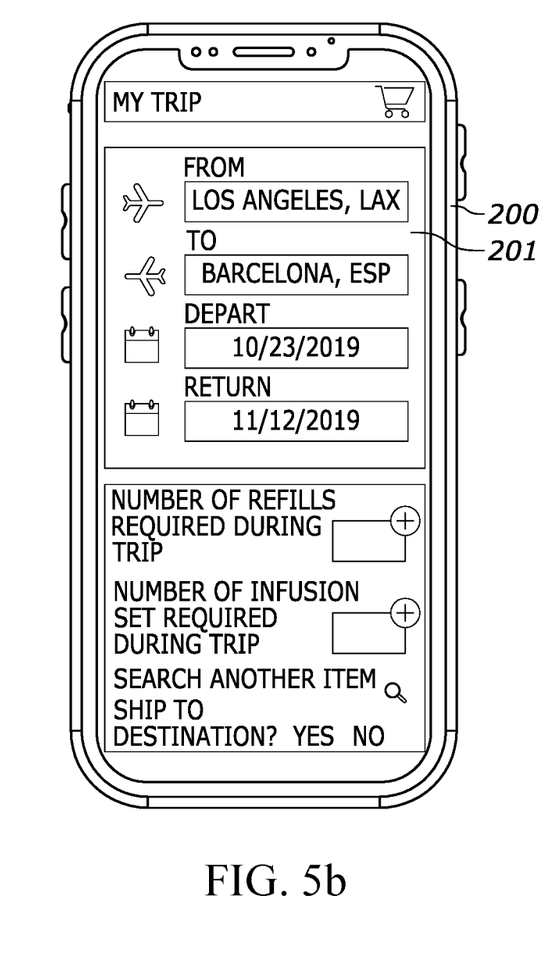

Referring to FIGS. 5a and 5b, an example method/device is shown whereby a mobile computing device 200 may be used to assist with ordering drug delivery device travel kits. For example, upon initiation of an application 201 within the portal, the patient may be asked to build a profile where they may select their current therapy, which may include a therapy type, a duration, and a volume. In some examples, IVSS 54 in the delivery container. This percentage may vary between approximately 0.5% to approximately 12% of the final volume in the delivery container. Further, citrate may increase the risk of glass delamination if filled in glass vials. In the event that citrate is necessary for drug product stabilization (determined on a per-product basis), the delivery containers may be constructed from CZ, other plastic compositions, or glass (using, for example, glass delamination control vial approaches). Other examples of ingredients for suitable IVSSs are possible. Suitable IVSS concentrations protect against protein-plastic interactions and/or surface adsorption, and more specifically, in the lower end of the concentration range where even minor losses may potentially change the effective dose. The below table illustrates example component concentrations for varying IVSS concentrations:

TABLE 1

| Component Concentrations with Varying IVSS Concentrations (top column units are V/v) % of IVSS | | | | | | | | |
|---|---|---|---|---|---|---|---|---|
| IVSS COMPONENTS | 0.5 | 1.0 | 2.0 | 4.0 | 6.0 | 8.0 | 10.0 | 12.0 |
| Lysine monohydrochloride (M) | 0.00625 | 0.0125 | 0.025 | 0.05 | 0.075 | 0.1 | 0.125 | 0.15 |
| Citrate Monohydrate (M) | 0.000125 | 0.00025 | 0.0005 | 0.001 | 0.0015 | 0.002 | 0.0025 | 0.003 |
| Polysorbate 80 (% w/v) | 0.0005 | 0.001 | 0.002 | 0.004 | 0.006 | 0.008 | 0.01 | 0.012 | the infusion tubing sets also may be specified as part of the therapy. Patients also have the ability to inform their doctors of their travel plans via this portal. Next, specific upcoming travel plans including durations and destination can be easily inserted into the portal, and the application 201 may automatically calculate the number of infusion therapy drug reservoirs/IV bags with the appropriate volumes. The corresponding tubing sets and the quantity required during the duration of travel can also be added into the user's shopping cart. Additionally, other accessories including sterile connectors and tubing sets can be added to the same travel kit. As a final step, the patient may select "ship to destination" and the travel kit will be prepared at the local pharmacy at destination and shipped to the patient in a timely manner.

In some examples, the IVSS may be provided as a percentage of an overall volume of solution. In these examples, suitable quantities of IVSS may range between approximately 2% and approximately 15% (e.g., between approximately 1 mL in a 50 mL container and approximately 25 mL in a larger, 270 mL container). The IVSS can also act as a pretreating surfactant or a buffering component that prevents adsorption of the drug onto the walls of the container. For example, due to the highly potent nature of some drugs being administered, if the container is not sufficiently and properly coated with the IVSS, it may lead to an undesirable risk of drug molecules adhering or adsorbing to the inner walls of the container. In the event of adsorption of the drug onto the delivery container walls, the dosage of the drug may be adversely impacted. In such a situation, it may be desirable to utilize the previously discussed example steps.

In some examples, the IVSS may include polysorbate. In some examples, the IVSS formulation may include approximately 1.25 M lysine monohydrocholoride, 25 mM citric acid monohydrate, 0.1% (wN) polysorbate 80, and has a pH of approximately 7.0. In other examples, the IVSS 54 may include similar formulations, but also have a minimum of approximately 0.9% NaCl and approximately 0.001 to approximately 0.1% (w/v) polysorbate 80. It is appreciated that different BiTEs® require different final percentages of By providing the components in containers that are selectively connectable, it may be no longer necessary to prepare a needle and syringe assembly to inject one component into another container, to ensure that this prepared needle and syringe assembly is sterilized, and/or to ensure a correct volume or amounts of components are added together.

Some conventional systems may provide delivery containers having saline solution overfill, where more saline solution is provided in the delivery container than what is needed for dosage. In these systems, it may be necessary to remove a volume of the saline solution prior to preparing the drug dosage, which may require preparing a sterile withdrawal tool (e.g., a needle and syringe assembly) and carefully extracting an accurate amount of saline solution. Conversely, the disclosed systems may additionally eliminate this process, as the containers are prefilled with the required quantity of components. Additionally, the risk of a needle sticking due to the transfer of the components may also be reduced or mitigated.

Additionally, many or all of the above described steps may be automated or semi-automated or reduced in time/scope, thereby potentially saving time and effort for the persons preparing and/or using the drug.

As discussed above, the drug product container contains a predetermined quantity of drug product or active pharmaceutical ingredient ("API") (e.g., between approximately 2 mcg and approximately 100 mcg), depending on the BiTE® and container size, which, in the illustrated example, is in powdered form (i.e., lyophilized) requiring reconstitution. In other examples, the drug product may be in liquid form and may not require reconstitution. Nonetheless, the system includes an accurate quantity of drug product, and thus does not require the need to add additional quantities thereto in a sterile environment. In some examples, the API may be in the form of a half-life extended ("HLE") BiTE® and/or an IV-admin monoclonal antibody ("mAbs) as desired. These HLE BiTEs® include an antibody Fc region that advantageously provides different drug properties such as longer and extended half-lives. Accordingly, such APIs may be preferred due to their ability to maintain protective levels in the patient for relatively longer periods of time. Nonetheless, in other examples, the API may be in the form of a canonical-BITE® that is to be administered in a professional healthcare environment.

In some embodiments, the drug delivery system may have an integrated reconstitution subsystem onboard to dilute a lyophilized drug into a liquid form. In certain such embodiments, a diluent reservoir may be included for storing a diluent solution and a lyophilized reservoir may be included storing a lyophilized compound separate from the diluent solution. Furthermore, a fluid drive mechanism may be included for mixing the diluent solution in the diluent reservoir with the lyophilized compound in the lyophilized reservoir. In some embodiments, the fluid drive mechanism may transfer the diluent solution from the diluent reservoir into the lyophilized reservoir and/or provide any circulation and/or agitation needed to achieve full reconstitution. In some embodiments, an additional final reconstituted drug reservoir may be included and serve as a delivery reservoir from which the reconstituted drug is discharged into the patient; whereas, in other embodiments, the lyophilized reservoir may serve as the delivery reservoir. While the reconstitution subsystem may be physically integrated into the drug delivery system in certain embodiments, in other embodiments the reconstitution subsystem may constitute a separate unit which is in fluid communication with the drug delivery system. Having a separate unit may simplify the reconstitution process for healthcare providers in certain cases.

The drug product container may be in the form of an IV bag, a vial, a prefilled syringe, or similar container that includes a reconstitution container body defining an inner volume. The inner volume may be sterile. In some approaches, the reconstitution container adapter may also be a CSTD (or, in examples where the prefilled reconstitution container is in the form of a syringe, the container adapter may be a needle) that mates, engages, and/or couples to the vial adapter. Additionally or alternatively, the drug product can be bulk lyophilized and filled into a cartridge or container that is typically used to administer with an IV pump. If needed the dehydrated forms of IVSS, NaCl, and any other components needed for the final administered solution can be bulk lyo'ed and filled into the cassette for long term storage.

The prefilled diluent container contains a predetermined quantity of diluent (e.g., preservative-free water for injection or "WFI") (e.g., between approximately 0.5 mL and approximately 10 mL) to be added to the prefilled drug product container for reconstitution of the drug product. In some examples, a benzyl alcohol preserved (or any other preservative) WFI may be used.

As previously noted, in some examples, the prefilled drug product container may be in the form of a prefilled syringe that contains the drug product. In these examples the drug product may be in the form of a liquid BiTE® formulation used in conjunction with a monoclonal antibody (mAb), In these examples, the drug product may be directly added to the delivery container without the use of a vial adapter system (such as the above-mentioned CSTDs) where more traditional needle-syringe injection/delivery into the container is preferred, which may advantageously simplify and/or improve supply chain and manufacturing control, and may further allow for more compact commercial packaging that takes up less space in storage systems at healthcare facilities. In these examples, the prefilled drug product vial may or may not need to be reconstituted prior to transferring the drug product to the delivery container.

The system may be distributed and/or sold as a common kit packaging, but other distribution/packaging is may be suitable. The drug product may be in the form of a half-life extended bispecific T cell engager (BITE®), but other drug products are suitable. The diluent include water for injection ("WFI"), but other diluents may be suitable. The containers may be pliable bags, such as IV bags, but other containers may be suitable. In some examples, one or more of the containers is in the form of an IV drip bag constructed from a plastic or other material, e.g., 250 mL 0.9% Sodium Chloride IV bag constructed of a suitable material such as polyolefin, non-DEHP (diethylhexl phthalate), PVC, polyurethane, or EVA (ethylene vinyl acetate) and can be filled to a volume of approximately 270 mL to account for potential moisture loss over long-term storage.

During some or all of the above steps, the contents of a container may then be gently stirred, swirled, and/or inverted to mix the ingredients, thereby forming a desired mixture. Similarly, the mixtures may be visually inspected for imperfections and/or to ensure adequate mixing has occurred.

The system may be used to provide intravenous, subcutaneous, intra-arterial, intramuscular, and/or epidural delivery approaches. By using the system, patient anxiety and or confusion may be reduced due to reduced preparation complexity and wait times caused by the drug preparation process.

In some examples, the prefilled delivery container is in the form of an IV drip bag constructed from a plastic or other material, e.g., 250 mL 0.9% Sodium Chloride IV bag constructed of a suitable material such as polyolefin, non-DEHP (diethylhexl phthalate) PVC, polyurethane, or EVA (ethylene vinyl acetate) and can be filled to a volume of approximately 270 mL to account for potential moisture loss over long-term storage. Other examples of suitable delivery containers are possible such as, for example, a glass bottle or container. Example suitable prefilled delivery containers are described in U.S. Appln. No. 62/804,447, filed on Feb. 12, 2019 and U.S. Appln. No. 62/877,286 filed on Jul. 22, 2019, the contents of each of which are incorporated by reference in their entirety.

At least one of the delivery container adapters may be a closed system transfer device ("CSTD") that allows for transfer of the drug and/or fluids into the container body. Example CSTD devices may include the OnGuard CSTD provided by B. Braun Medical Inc, BD PhaSeal CSTD components, Equashield CSTD, Codon CSTD, and the like. Further, non-closed system transfer devices may be used such as West Pharmaceuticals vial and bag adapters. Other examples are possible. The prefilled delivery container may include any number of delivery container adapters having different specifications (e.g., port sizes) to accommodate the use of different drug product vials.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Nontherapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4I37 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution;

Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™ Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α581 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCG8 mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TI MP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF a monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-14(R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl) ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798

(rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a $KRAS^{G12c}$ small molecule inhibitor, or another product containing a $KRAS^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA) x anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1 x IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33 x anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3) x anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP x 4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19 x CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3 x epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33 x anti-CD3 BiTE® (bispecific T cell engager) construct. In some embodiments, the drug delivery device may contain or be used with AMG 701 or another product containing a half-life extended (HLE) anti-B-cell maturation antigen (BCMA) x anti-CD3 BiTE® (bispecific T cell engager) construct. In some embodiments, the drug delivery device may contain or be used with AMG 757 or another product containing a half-life extended (HLE) anti-delta-like ligand 3 (DLL3) x anti-CD3 BiTE® (bispecific T cell engager) construct. In some embodiments, the drug delivery device may contain or be used with AMG 910 or another product containing a half-life extended (HLE) epithelial cell tight junction protein claudin 18.2 x CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery system comprising:
   a packaging housing;
   a first component including at least one of a drug product, a diluent, a saline solution, or an IV stabilizing solution ("IVSS"), wherein the first component is disposed in a first container in a storage state and the first container is positioned in a first compartment of the packaging housing;
   a second component including at least one of the drug product, the diluent, the saline solution, or the IVSS, wherein the first component is different than the second component and the second component is disposed in a second container in a storage state and the second container is positioned in a second compartment of the packaging housing;
   wherein each of the first compartment and the second compartment includes an individual seal; and
   a third component including at least one of the drug product, the diluent, the saline solution, and the IVSS, wherein the third component is different than the first component and the second component, wherein the third component is disposed in a third container in a storage state and the third container is positioned in a third compartment of the packaging housing,
   wherein the packaging housing defines a housing bottom surface at least one of the first, second, and third compartments has a compartment bottom surface that is non-parallel to the housing bottom surface to facilitate removal of air bubbles.

2. The drug delivery system as in claim 1, wherein at least one of the first, second, and third containers comprises an IV bag, and wherein the packaging housing includes at least one port holder configured to secure at least one port of the IV bag in a storage position, and wherein the port holder is removable from the packaging housing to facilitate removal of the IV bag from the packaging housing.

3. The drug delivery system as in claim 1, wherein the packaging housing includes a stand for supporting instructions for use.

4. The drug delivery system as in claim 1, wherein the drug product delivery is packaged as a kit.

5. The drug delivery system as in claim 4, wherein the kit further includes a second packaging housing, wherein at least one of the first and second packaging housing is configured to be maintained under refrigerated conditions and the other of the first and second packaging housing is configured to be maintained at about room temperature.

* * * * *